United States Patent
Richter

(10) Patent No.: US 6,736,838 B1
(45) Date of Patent: May 18, 2004

(54) METHOD AND APPARATUS FOR COVERING A STENT

(75) Inventor: Jacob Richter, Ramat Hasharon (IL)

(73) Assignee: Zuli Holdings Ltd., Tel-Aviv (IL)

( * ) Notice: Subject to any disclaimer, the term of this patent is extended or adjusted under 35 U.S.C. 154(b) by 0 days.

(21) Appl. No.: 09/532,653

(22) Filed: Mar. 22, 2000

(51) Int. Cl.⁷ .................................................. A61F 2/06
(52) U.S. Cl. ...................................................... 623/1.11
(58) Field of Search ............................. 606/1, 108, 194, 606/195, 198, 200; 623/1.13, 1.23, 1.47, 1.41, 1.21, 1.44

(56) References Cited

U.S. PATENT DOCUMENTS

| | | |
|---|---|---|
| 4,755,593 A | 7/1988 | Lauren |
| 5,037,377 A | 8/1991 | Alonso |
| 5,376,110 A | 12/1994 | Tu et al. .................... 623/12 |
| 5,510,077 A | 4/1996 | Dinh et al. |
| 5,554,182 A | 9/1996 | Dinh et al. |
| 5,571,166 A | 11/1996 | Dinh et al. |
| 5,575,818 A | 11/1996 | Pinchuk ..................... 606/195 |
| 5,591,224 A | 1/1997 | Schwartz et al. |
| 5,595,571 A | 1/1997 | Jaffe et al. |
| 5,628,785 A | 5/1997 | Schwartz et al. |
| 5,653,747 A | 8/1997 | Dereume |
| 5,693,085 A | 12/1997 | Buirge et al. |
| 5,718,159 A * | 2/1998 | Thompson .................. 87/33 |
| 5,720,777 A | 2/1998 | Jaffe et al. |
| 5,800,507 A | 9/1998 | Schwartz |
| 5,843,158 A | 12/1998 | Lenker et al. |
| 5,843,180 A | 12/1998 | Jaffe et al. |
| 5,843,181 A | 12/1998 | Jaffe et al. |
| 5,849,034 A | 12/1998 | Schwartz |
| 5,865,723 A | 2/1999 | Love ........................ 623/12 |
| 5,895,407 A | 4/1999 | Jayaraman |
| 6,187,039 B1 | 2/2001 | Hiles et al. ................ 623/1.44 |
| 6,254,627 B1 * | 7/2001 | Freidberg ................. 623/1.11 |

FOREIGN PATENT DOCUMENTS

| | | |
|---|---|---|
| DE | 299 17 306 | 3/2000 |
| DE | 29917306 U1 | 4/2000 |
| EP | 0 328 401 A1 | 8/1989 |
| WO | 95/29647 A2 | 11/1995 |
| WO | WO 97/25002 | 7/1997 |
| WO | WO 99/15105 | 4/1999 |

* cited by examiner

*Primary Examiner*—Vy Bui
(74) *Attorney, Agent, or Firm*—Kenyon & Kenyon

(57) ABSTRACT

An expandable stent suitable for implantation in a lumen is covered with a biological material. In one embodiment, biological fibers are interwoven to form a stent covering. The fibers are disposed at an angle with respect to the longitudinal axis of the stent so that when the stent is expanded, the angle increases. In another embodiment, a strip of pericardium is helically wound around a supporting stent while the stent is in a compressed state. When the stent is expanded, the strip unwinds, but maintains full coverage of the stent. Interlocking edges may be formed on the strip of pericardium to maintain full coverage of the stent.

4 Claims, 2 Drawing Sheets

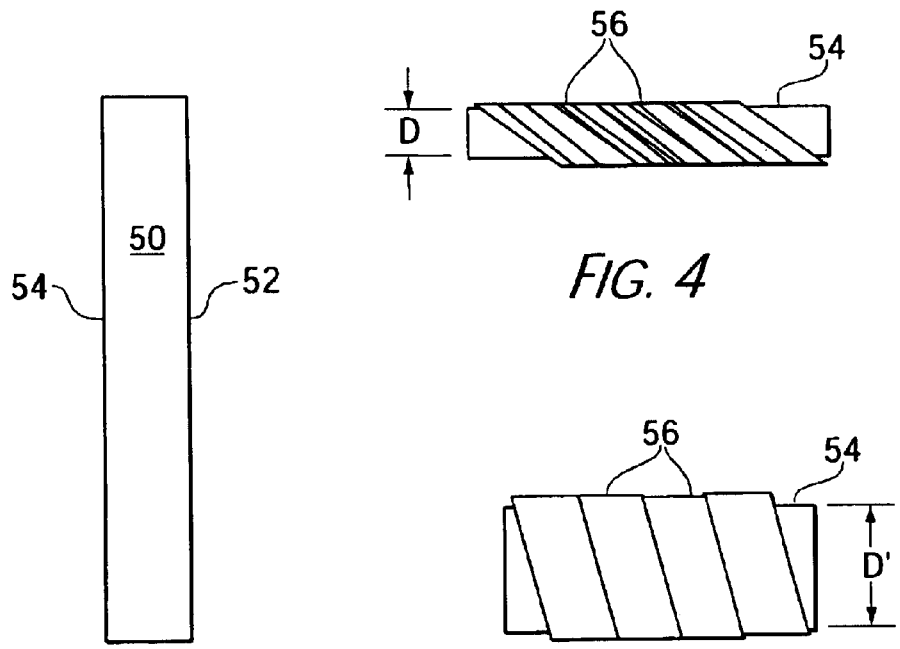
FIG. 3
FIG. 4
FIG. 5
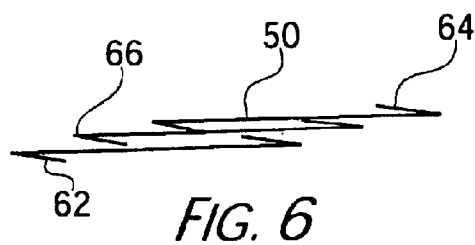
FIG. 6
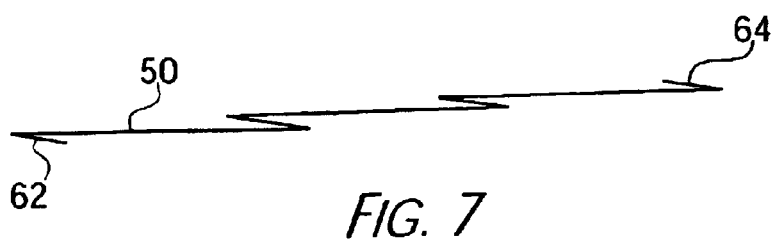
FIG. 7

METHOD AND APPARATUS FOR COVERING A STENT

FIELD OF THE INVENTION

The present invention relates generally to stents for implanting into a living body. In particular, the present invention relates to a biological covering for a stent suitable for implanting into a variety of lumens.

BACKGROUND OF THE INVENTION

In an attempt to prevent restenosis, metallic vascular stents have been permanently implanted in coronary or peripheral vasculature. These stents are typically delivered intraluminally by a catheter and expanded in place to support a diseased portion of an artery.

One shortcoming of these conventional stents is that even after stent implantation, restenosis can still occur. Another shortcoming is that during the implantation of the stent, the stent may cause particles to discharge from the artery wall through the open cell. These dislodged particles can embolize in the bloodstream, and may cause catastrophic effects.

In an attempt to reduce these problems, coverings have been proposed for stents. These coverings have been made from artificial materials, such as PTFE. As of yet, however, coverings made from artificial materials have not proven successful. This may be because of the poor biocompatibility of such materials.

There is also some experience using biological tissue such as bovine pericardium to build a covering for a stent that is more biocompatible than coverings made from artificial materials. Preliminary results with bovine pericardium have been encouraging from the point of view of biocompatibility.

The current method, however, of creating a covering using biological tissue is simplistic. A rectangular piece of pericardium is harvested from a bovine source. The pericardium is then, after being prepared so that it is suitable for implantation, rolled into a cylinder. The abutting edges of the pericardium are sewn together to create a covering. This covering is then placed over a stent.

There is an inherent disadvantage in this cut and sew approach to creating a covering. Biological tissue has a very small expansion range. Therefore, the diameter of the cut and sewn cylinder of tissue is limited to a very small range. This limits the stent to a very small range of expansion diameters, limiting the utility of the stent. This also limits the difference in diameter between the stent as delivered and the stent at its expanded state, increasing significantly the profile of the delivery system required for a given supported diameter.

SUMMARY OF THE INVENTION

In one embodiment of the present invention, biological fibers or biodegradable fibers or fiber groups are arranged as interwoven threads to make an expandable tube. The interwoven threads are arranged with an acute angle between the interwoven threads while the stent is unexpanded. When the stent is expanded, the angle between the interwoven threads increases. This allows the stent covering to be expanded to a variety of diameters.

In another embodiment, a strip of pericardium is helically wound around a stent with a substantial overlap between adjacent windings while the stent is in a first, unexpanded diameter. During expansion to a second expanded diameter, the strips will slide over the stent and unwrap for a smaller number of loops, but will still completely cover the stents. In a further enhancement to this embodiment, the edges of the spiral wrapping are formed into locking folds to prevent the spiral loops from separating during expansion of the stent and covering.

Accordingly, it is an object of the current invention to provide an improved biological tissue covering for a stent, and a method for producing the same.

Further objectives and advantages of the subject invention will be apparent to those skilled in the art from the detailed description of the disclosed invention.

BRIEF DESCRIPTION OF THE DRAWINGS

FIG. 3 shows a strip of pericardium used to form a stent covering.

FIG. 4 shows a spiral wrapped stent covering in an unexpanded state.

FIG. 5 shows a spiral wrapped stent covering in an expanded state.

FIG. 6 shows a partial cross-sectional view of one embodiment of a spiral wrapped stent covering in an unexpanded state.

FIG. 7 shows a partial cross-sectional view of one embodiment of a spiral wrapped stent covering in an expanded state.

DETAILED DESCRIPTION OF PREFERRED EMBODIMENTS

The subject invention will now be described in detail for specific preferred embodiments of the invention, it being understood that these embodiments are intended only as illustrative examples and the invention is not to be limited thereto.

Figure 1:
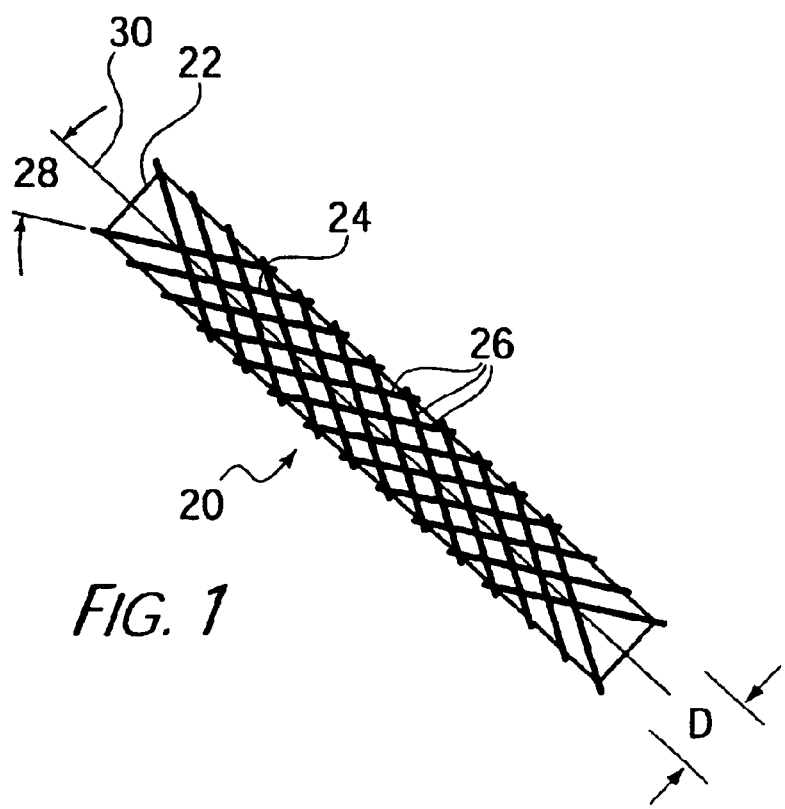
FIG. 1 shows an interwoven stent covering in an unexpanded state.
Figure 2:
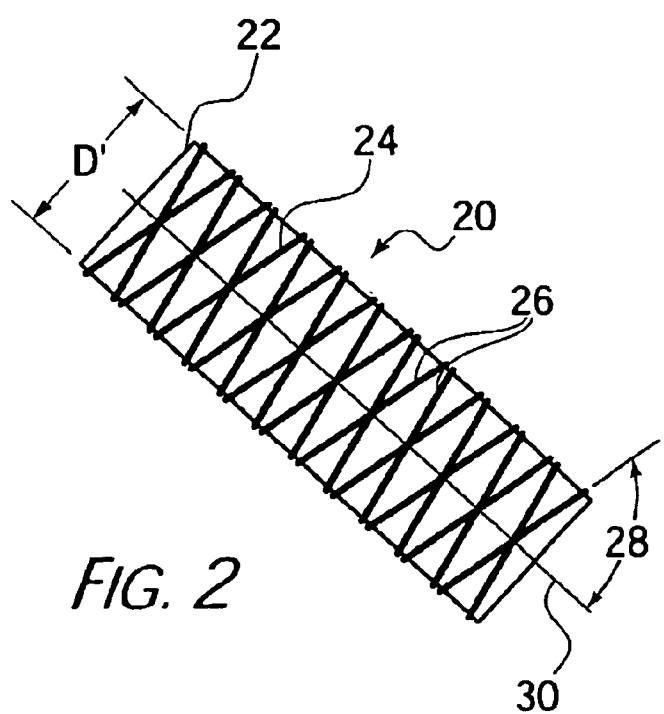
FIG. 2 shows an interwoven stent covering in an expanded state.

FIGS. 1 and 2 show an endoprostheses according to this invention. A luminal endoprostheses 20 has a tubular stent 22 expandable from a first diameter D shown in FIG. 1 to a second diameter D' shown in FIG. 2. Stent 1 may be a self-expanding stent or a balloon expandable stent. One example of a suitable balloon expandable stent is illustrated in U.S. Pat. No. 5,807,404, the disclosure of which is hereby incorporated by reference.

The stent has a covering 24 formed of biological fibers. The biological fibers may be obtained by dissolving any suitable biological tissue, such as bovine, ovine, or porcine pericardium tissue. Alternatively, the fibers can be formed from other material, such as Cut-Gut collagen threads.

As shown in FIG. 1, the individual fibers 26 are interwoven, and form an angle 28 with respect to the longitudinal axis 30 of the stent 22. When the stent is at the unexpanded diameter D, the angle 28 is approximately 30°.

Typically, the endoprostheses will be implanted using a conventional balloon angioplasty procedure. In this procedure, the stent 22 and associated covering 24 are placed onto the balloon at the end of a balloon catheter and delivered to the site of the restricted or diseased portion of an artery. The stent and covering are then expanded into contact with the lumen by inflating the balloon. The catheter can then be deflated and withdrawn, leaving the stent and covering at the treatment site. As shown in FIG. 2, upon expansion from the first diameter D to the second diameter D', the fibers of the expandable coating change orientation so that they are at a greater angle 28 with respect to the longitudinal axis 30 of the stent 20 then when they are in the first diameter D. The angle 28 at the expanded diameter D' is dependent upon the amount of expansion of the stent. Therefore, depending on the size of the lumen which the stent is inserted into, the angle 28 varies from 30° to 90°.

Another embodiment of the biological stent covering is shown in FIGS. 3–5. In this embodiment, pericardium tissue is collected and prepared in a manner known to those skilled in the art. The pericardium tissue is then cut into a single strip 50 with lateral edges 52. A supporting stent 54 with an unexpanded diameter of D and an expanded diameter of D' is provided. The strip 50 is helically wound around a supporting stent 54 while the stent is in a collapsed state with a diameter of D to form a series of helical windings 56. The lateral edges 52 of adjacent helically windings 56 are arranged so that the lateral edge 52 of one winding overlaps the adjacent winding.

Upon expansion of the stent from the diameter D to D', the helically wound strip of pericardium unwinds. However, because of the overlap between adjacent strips, no area of the stent is uncovered during and after expansion of the stent and covering. The ratio between the maximal expanded diameter without causing gaps, and that of the unexpanded stent equals the overlap ratio of the stent.

An alternative embodiment of the spiral wrapped stent is shown in FIGS. 6 and 7. In this embodiment, the edges 52 of the pericardium strip 50 are provided with interlocking edges 60, 62. The right interlocking edge 62 is formed by folding the edge of the pericardium strip over itself. The left interlocking edge 64 is formed by folding the edge of the pericardium strip over itself; the left edge is folded in the opposite direction as the right edge.

The strip with the interlocking edges is helically wound around the stent in the same manner as described above with respect to the embodiment illustrated in FIGS. 4 and 5. Special care is taken to make sure that the right interlocking edge 62 is placed between the right edge 66 and the left interlocking edge 64 of the adjacent spiral wrap. Upon expansion of the stent, the right and left interlocking edges mate together. In this manner, the interlocking edges assure that there is no gaps in the coverage of the expanded stent, as illustrated in FIG. 7.

What is claimed is:

1. A covered stent comprising:

an expandable stent with a longitudinal axis, the stent being expandable from a first diameter to a second diameter, said stent having an outer surface;

a covering affixed to the outer surface of the stent along its length, the cover being formed of braided linear threads of biological material, selected from the group consisting of: bovine pericardium, ovine pericardium, porcine pericardium, wherein in the first diameter, the biological threads form a first angle with respect to the longitudinal axis of the stent, and in the second diameter, the biological threads form a second angle with respect to the longitudinal axis of the stent.

2. The stent according to claim 1, wherein the first angle is approximately 30°.

3. The stent according to claim 1, wherein the second angle is dependent upon the amount of expansion of the stent.

4. An intraluminal stent, comprising:

a tubular support member with a longitudinal axis; the member being expandable from a first diameter to a second diameter, the member having an outer surface, an expandable covering applied over the outer surface of the tubular support member along its length, the expandable covering being made from braided linear threads of pericardium fibers, the threads arranged so that in the first diameter, the threads are at an angle of less than 45 degrees with respect to the longitudinal axis of the tubular support member.

* * * * *